United States Patent [19]

Kundson, Jr.

[11] Patent Number: 4,825,855

[45] Date of Patent: May 2, 1989

[54] INTERCOURSE AIDING APPARATUS

[76] Inventor: Kenneth C. Kundson, Jr., c/o Sybaris Clubs International, Inc., 3350 Milwaukee Rd., Northbrook, Ill. 60062

[21] Appl. No.: 177,857

[22] Filed: Mar. 22, 1988

Related U.S. Application Data

[63] Continuation of Ser. No. 912,272, Sep. 29, 1986, abandoned.

[51] Int. Cl.$^4$ .............................................. A61F 5/41
[52] U.S. Cl. .................................. 128/79; 128/845; 297/277
[58] Field of Search ................... 128/79, 845; 272/85; 297/277, 278; D6/344, 347

[56] References Cited

U.S. PATENT DOCUMENTS

| D. 244,068 | 4/1977 | Styron, Jr. | D6/347 |
| D. 254,458 | 3/1980 | Wakefield | D6/347 |
| D. 268,232 | 3/1983 | Scales | D6/347 |
| D. 278,292 | 4/1985 | Newby | D6/347 |
| D. 281,206 | 11/1985 | Halsall | D6/347 |
| 265,611 | 8/1882 | Knudson | 248/317 |
| 688,368 | 12/1901 | Waddel | 297/278 |

FOREIGN PATENT DOCUMENTS 2140008  2/1973  Fed. Rep. of Germany ........ 128/79

OTHER PUBLICATIONS

Penthouse, Jul. 1981 issue, pp. 94, 97.
Cramer, Gerald; *Sewer of Six*, pp. 110–115.

*Primary Examiner*—Gene Mancene
*Assistant Examiner*—Cary E. Stone
*Attorney, Agent, or Firm*—Wood, Dalton, Phillips, Mason & Rowe

[57] ABSTRACT

An apparatus is provided for use in performing intercourse, including a rigid frame supported above a bed, an elongate panel of cloth, and cables suspending the cloth panel from the frame. The cloth panel is suspended from the frame such that an opening therein near one end is substantially at the lowest portion of the the cloth panel whereby the opening exposes the genitalia of a user seated thereon in a spaced relation above the bed. The cloth panel is broader at its one end than at its other end.

11 Claims, 1 Drawing Sheet

U.S. Patent
May 2, 1989
4,825,855
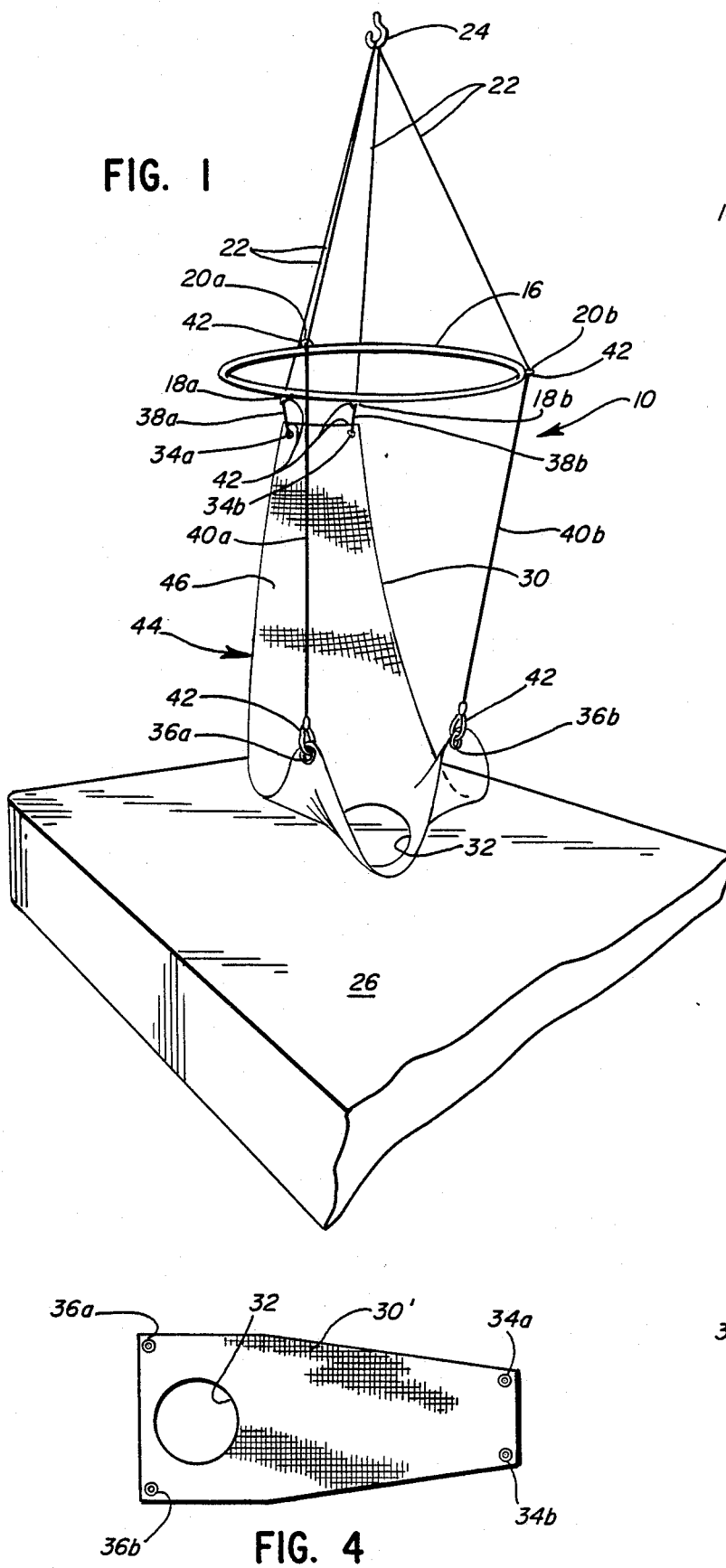
FIG. 1
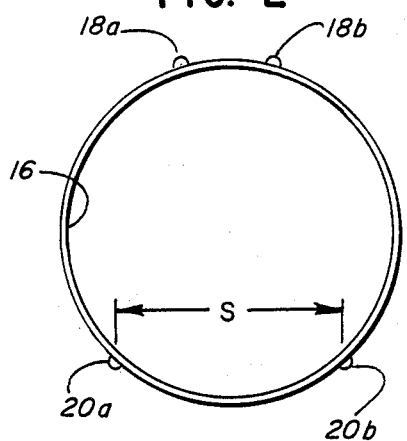
FIG. 2
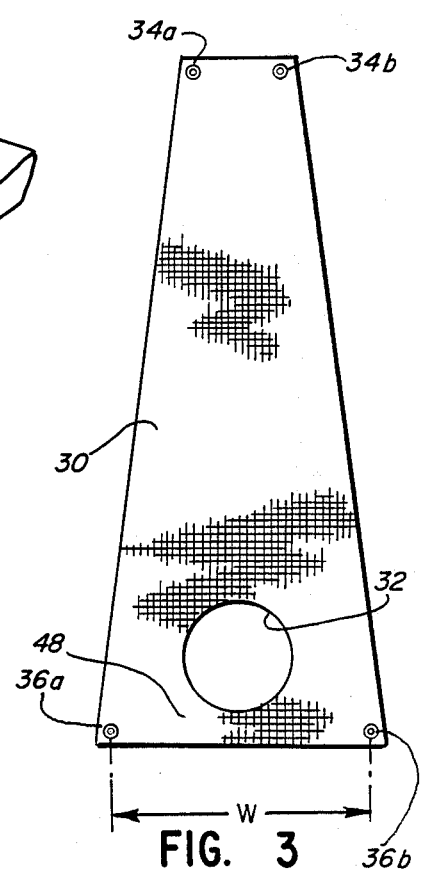
FIG. 3
FIG. 4

– 1 –

INTERCOURSE AIDING APPARATUS

This application is a continuation of application Ser. No. 912,272, filed Sept. 29, 1986, now abandoned.

DESCRIPTION

1. Technical Field

This invention relates generally to a sexual performance aid and more particularly to an apparatus for use in performing intercourse.

2. Description of the Prior Art

A large variety of sexual aids are, of course, known in the art. Some of these aids directly physically stimulate a participant, while others aid the positioning of the participants in their direct physical stimulation of one another.

A common position which many people find to be erotic is with the woman on top of and straddling the man. A variation on this position which has also been found to be erotic is one in which the woman supports herself so that her thighs and buttocks do not contact the man, with the only direct contact between the two being the contact of the penis with the female genitalia. However, since this position can be tiring for a woman supporting herself above the man, a support has sometimes been employed such as shown in my own U.S. Pat. No. Des. 265,611. This support has been found to have several disadvantages, however, as it is difficult to clean, is somewhat uncomfortable to sit in, and its stiff seat hinders motion by both the man and woman.

The present invention is directed toward overcoming one or more of the problems as set forth above.

SUMMARY OF THE INVENTION

In one aspect of the present invention, an apparatus is provided for use in performing sexual intercourse, including a rigid frame supported above a bed, an elongate panel of cloth, and means for suspending the cloth section from the frame. The cloth panel is suspended from the frame such that an opening therein near one end is substantially at the lowest portion of the cloth panel whereby the opening exposes the genitalia of a user seated thereon in a spaced relation above the bed. The cloth panel is broader at its one end than at its other end.

One object of the present invention is to provide an apparatus which aids a couple in performing sexual intercourse. Another object of the present invention is to allow a couple to perform sexual intercourse for a long period of time with the woman on top without tiring the woman. Still another object of the present invention is to provide a seat support which exposes the genitalia of the person seated thereon such that a partner may contact the genitalia to stimulate one another. Yet another object of the present invention is to provide a seat as described which is comfortable during use and which allows free motion to allow a couple to freely stimulate one another according to their particular tastes.

BRIEF DESCRIPTION OF THE DRAWINGS

FIG. 1 is a perspective view of the apparatus showing a couple in phantom;

FIG. 2 is a view of a ring usable with the apparatus;

FIG. 3 is a plan view of the panel of the apparatus laid flat; and

FIG. 4 is a plan view of an alternative panel.

DESCRIPTION OF THE PREFERRED EMBODIMENT

The intercourse aiding apparatus 10 comprising the present invention is shown in FIG. 1. The apparatus 10 includes a ring 16 (see FIG. 2) having spaced hooks or eyes 18a,18b, 20a,20b thereon. The eyes 18a,18b,20a,20b come in two pairs, one pair 18a,18b being more closely spaced than the other 20a, 20b.

The ring 16 is suspended in a generally horizontal position by cords 22 secured to the eyes 18a,18b,-20a,20b, said cords 22 being suitably suspended from a ceiling (as by the hook support 24 shown) over a bed 26.

The apparatus 10 further includes a flexible panel 30 (see FIG. 3) which is generally an elongate trapezoid having an opening 32 adjacent the wide front end 48. A panel 30 measuring substantially 48½ inches along each side, 20½ inches on the wide end, and 8 inches on the narrow end, with an 8 inch diameter opening, has been found to be particularly suitable.

The panel 30 is preferably formed of a sturdy, soft and washable cloth material such as nylon. Reinforced grommets 34a,34b,36a,36b are provided in the corners of the panel 30.

As seen in FIGS. 2 and 3, the spacing S between the eyes 20a and 20b is less than the spacing W between the grommets 36a and 36b at the opposite ends of the flexible front end portion 48.

An alternative panel 30' which may also be used is shown in FIG. 4. The sides of the panel 30' adjacent the opening 32 are parallel and tapered to the narrow end thereafter.

Suitable cords 38a,38b suspend the narrow end of the cloth panel 30 adjacent the ring 16 from one pair of eyes 18a,18b. Longer cords 40a,40b suspend the wide end of the cloth panel 30 spaced from the ring 16 from the other pair of eyes 20a,20b so that the opening 32 is at substantially the lowest part of the catenary shape of the cloth panel 30. Preferably, the cords 22,38a,38b,40a,40b should be metal or other nonstretching cables suitably covered by plastic or the like to protect the couple. Further, it is preferred that the cords 38a,38b,40a,40b have quick releasing swivel hooks 42 which securely connect to the grommets 34a,34b,36a,36b and eyes 18a,18b,20a,20b yet allow for easy removal for washing.

Preferably, the wide end of the cloth panel 30 is wider (when laid flat as in FIG. 3) than the spacing of the front set of eyes 20a,20b, as this configuration allows the cloth panel 30 to define a form-fitting and properly supporting seat 44 and seat back 46 as shown in FIG. 1.

The apparatus 10 as described above is thus readily usable to aid a couple having sexual intercourse. The woman sits in the seat 44 facing the cords 40a,40b and spreads her legs so that they extend outside of the cords 40a,40b. In this manner, her genitalia are downwardly exposed through the opening 32 for contact with her male partner laying beneath her on the bed 26, and her feet are rested on the bed 26 so that she may rock herself slowly, or otherwise move according to her and her partner's sexual tastes. Further, the woman may lean back against the seat back 46 so as to not only sit comfortably but also to slightly change the height and angle of her exposed genitalia (by changing the catenary shape of the seat 44) to provide variety to the stimulation between partners.

The apparatus 10 may also be used in a variety of ways other than that described by, for example, extending the woman's legs between the cords 40a,40b and allowing her partner to hold her legs and control her movement.

It is readily apparent from the description that the apparatus 10 is comfortable for the person seated therein and allows free motion of that person so that the couple may enjoy uninhibited sexual pleasure. Still further, the cloth panel 30 of the apparatus 10 can be easily detached for cleaning between uses (a particularly important feature in those locations where the apparatus is used by more than one couple).

Other aspects, objects and advantages of the present invention can be obtained by a study of the drawings, the specification and the claims.

I claim:

1. An apparatus for use in performing intercourse, comprising:
   a rigid frame supported above a surface;
   an elongate flexible panel broader at one end than the other, said panel having an opening therein near said one end, said one end having a flexible front edge portion, said panel further having a rear edge portion; and
   means for suspending the panel from the frame with the opening substantially at the lowest portion of the panel whereby the opening exposes the genitalia of a user seated thereon in a spaced relation above the surface, said suspending means comprising means having a first portion connected to said rear edge portion, and a second portion connected to opposite ends of said flexible front edge portion of the panel for urging said opposite ends toward each other as a function of the user setting on said one end of the panel, and yieldably urging apart the legs of a user when seated on said one end of the panel with the user's legs outwardly of said suspending means.

2. The apparatus of claim 1, wherein the panel is a quadrilateral with four corners, the two corners at said other end being secured close to the frame and the two corners at said one end being suspended from the frame by two laterally spaced cords, said panel thereby also forming a back support for a user seated thereon.

3. The apparatus of claim 2, wherein the cords are plastic covered metal cables.

4. The apparatus of claim 2, wherein the cords have swivel hooks for securing to the panel.

5. The apparatus of claim 2, wherein the panel is substantially 48½, 20½, 48½, and 8 inches along its sides, said opening is substantially circular with an 8 inch diameter, and said ring is substantially 24 inches in diameter.

6. The apparatus of claim 1, wherein the suspending means are adapted for easy detachment from the panel.

7. The apparatus of claim 1, wherein the suspending means supports the panel in a substantially catenary shape with the opening substantially at the lowest portion of the shape.

8. The apparatus of claim 1, wherein the frame is suspended from a ceiling.

9. The apparatus of claim 1, wherein the panel is nylon cloth.

10. The apparatus of claim 1, wherein the panel has a rectangular portion about the opening and is tapered therefrom to the narrower other end.

11. An apparatus for use in performing intercourse, comprising:
    a rigid ring suspended from a ceiling above a bed and disposed in a substantially horizontal plane, said ring having first and second pairs of eyes fixed thereon, said first pair being spaced apart a distance S;
    a pair of cables depending from eyes of the first pair of eyes;
    an elongate quadrilateral panel of flexible cloth having one end defining corners spaced apart a width W greater than spacing S, each corner at the one end being secured to a respective one of the cables, and each corner at the other end being secured to respective ones of the second pair of eyes, said cloth panel further having an opening therein near its one end and at substantially the lowest portion of the suspended cloth panel whereby the opening exposes the genitalia of a user seated thereon in a spaced relation above the bed, said cables cooperating with the panel of cloth to comprise means for urging said opposite ends toward each other as a function of the user setting on said one end of the panel, and yieldably urging the legs of a user apart when seated on said panel with the user's legs outwardly of said cables.

* * * * *